United States Patent [19]

Enzmann et al.

[11] Patent Number: 4,468,224
[45] Date of Patent: Aug. 28, 1984

[54] SYSTEM AND METHOD FOR CATHETER PLACEMENT IN BLOOD VESSELS OF A HUMAN PATIENT

[75] Inventors: Dieter R. Enzmann, Mountain View; Ingemar Lundquist, Oakland, both of Calif.

[73] Assignee: Advanced Cardiovascular Systems, Inc., Mountain View, Calif.

[21] Appl. No.: 343,435
[22] Filed: Jan. 28, 1982
[51] Int. Cl.$^3$ .............................................. A61M 5/00
[52] U.S. Cl. .................................... 604/247; 604/283; 604/164; 604/170
[58] Field of Search .................... 604/51-53, 604/93, 104, 122, 126, 158, 161, 164, 168, 169, 177, 247, 264, 272, 274, 283, 284, 900, 165, 167, 246; 137/843, 528, 533.17, 533.19; 251/358

[56] References Cited

U.S. PATENT DOCUMENTS

| | | | |
|---|---|---|---|
| 2,781,778 | 2/1957 | Lisciani | 251/358 |
| 2,888,238 | 5/1959 | Leathers et al. | 251/358 |
| 3,419,041 | 12/1968 | Jennings | 137/533.19 |
| 3,508,576 | 4/1970 | Gross | 251/358 |
| 3,797,486 | 3/1974 | Shaps | 604/93 |
| 3,859,998 | 1/1975 | Thomas et al. | 604/168 |
| 3,906,932 | 9/1975 | Ayres | 604/274 X |
| 3,934,576 | 1/1976 | Danielsson | 604/169 X |
| 3,942,916 | 3/1976 | de Leeuw | 137/843 |
| 4,016,879 | 4/1977 | Mellor | 604/164 X |
| 4,030,495 | 6/1977 | Virag | 604/126 X |
| 4,141,379 | 2/1979 | Manske | 604/246 |
| 4,193,399 | 3/1980 | Robinson | 604/900 X |
| 4,200,096 | 4/1980 | Charvin | 604/164 |
| 4,230,123 | 10/1980 | Hawkins, Jr. | 604/51 X |
| 4,231,367 | 11/1980 | Rash | 604/165 |
| 4,269,186 | 5/1981 | Loveless et al. | 604/168 |
| 4,305,395 | 12/1981 | Martinez | 604/165 X |
| 4,306,562 | 12/1981 | Osborne | 604/164 X |
| 4,310,017 | 1/1982 | Raines | 604/247 X |
| 4,354,492 | 10/1982 | McPhee | 604/247 |

FOREIGN PATENT DOCUMENTS

| | | |
|---|---|---|
| 2507119 | 9/1976 | Fed. Rep. of Germany . |
| 111639 | 8/1944 | Sweden ......................... 137/533.19 |

OTHER PUBLICATIONS

United States Catheter and Instrument Corporation, "Cardiovascular Catheters and Accessories," 1967-1968, Glens Falls, New York p. 29.

Primary Examiner—C. Fred Rosenbaum
Assistant Examiner—Michelle N. Lester
Attorney, Agent, or Firm—Flehr, Hohbach, Test, Albritton & Herbert

[57] ABSTRACT

A kit of instruments for percutaneous introduction of a catheter into a major blood vessel of a human patient, including a hollow needle assembly having a proximal end adapted to be inserted through the skin of a patient into the blood vessel, a guide wire adapted to be inserted through the needle into the blood vessel, and a catheter having a proximal end adapted to be inserted into the blood vessel over the guide wire after said needle is withdrawn over said guide wire. The hollow needle assembly includes a first small gauge hollow needle having a beveled needle point on the front end thereof, and at least a second hollow needle mounted concentrically over the first needle and having a sharp chisel-shaped front edge located a moderate distance behind the point on said first needle. The needle assembly further comprises a pair of outboard wings mounted thereto and adapted to be readily grasped for inserting said needle into the blood vessel; and a transparent backbleeding evaluation housing mounted to the rear of said needle assembly, the backbleeding housing has an internal chamber communicating with the interior bore of the first needle and is adapted to be filled with blood from said blood vessel when the point of said needle assembly is inserted therein. The backbleeding chamber has a rear port adapted to admit the guide wire for insertion through the internal bore of the needle into the blood vessel. A hydrophobic filter element is sealed into the rear port to permit air within the internal chamber to escape therefrom as blood enters from the blood vessel. The filter element is a thin membrane readily pierceable by the guide wire to admit the guide wire into the internal chamber without substantial loss of blood therefrom. A y-connector with one way valves in inlet arms is provided for communicating fluid into the catheter.

3 Claims, 25 Drawing Figures

SYSTEM AND METHOD FOR CATHETER PLACEMENT IN BLOOD VESSELS OF A HUMAN PATIENT

This invention relates generally to systems for placing catheters into major blood vessels of a human patient, and specifically, in one aspect to systems and methods for catheter placement and delivery of radiographic contrast media (hereafter simply referred to as contrast media) for performing angiographic or arteriographic studies. This invention specifically comprises an improvement over the general principles of the invention set forth in a copending commonly assigned patent application of Enzmann and Brody, Ser. No. 343,448, filed Jan. 28, 1982, now abandoned.

Placement of a catheter into a major blood vessel of a human patient may be performed for a variety of medical theraputic or diagnostic purposes. For example, percutaneous insertion of a catheter into the jugular or subclavian vein is often performed to enable measurement of central venous pressure or to facilitate total intravenous feeding or other intravenous therapy. In addition, percutaneous insertion of the catheter into an antecubital vein may be performed for any of these same purposes. It is also common to perform a percutaneous insertion of a catheter into a femoral artery or vein in the groin area of the patient to deliver contrast media for purposes of performing angiographic or arteriographic studies.

Until recently, angiographic or arteriographic x-ray studies have involved an expensive, highly invasive, in-patient procedure involving catheterization of the femoral artery and delivery of iodinated contrast media directly into the artery or organ of interest while performing x-ray film studies of various arterial structures within a human patient. Numerous types and locations of occlusive vascular disease have been studied using x-ray film angiographic techniques. Because of the limited sensitivity of x-ray film and because of the typically large degree of overlying or underlying structures which tend to obscure the desired portion of the image, high concentrations of contrast media are required, necessitating direct injection of undiluted contrast media into the artery through selective catheterization of that artery. Because of the in-patient nature of these techniques, this diagnostic regimen is quite expensive, and because of the concentration of contrast media and arterial catheterization, substantial risks of complications are inherent in this x-ray film diagnostic procedure.

Within the past several years dramatic advances have been made in computerized radiography in general and fluoroscopy digital subtraction angiography in particular. Digital subtraction angiography basically involves the combination of an x-ray generator with an x-ray sensitive, image intensifier whose output is viewed by a television camera with the video signal from the television camera digitized for storage in an image memory which can then be processed by general purpose digital computer. Utilizing a pre-injection or post-injection mask image of the area of vascularity to be studied and thereafter subtracting the mask image from the image obtained during contrast injection eliminates to a large degree obscuring background information in the image providing substantially improved contrast and visualization of the vascularity which is infused with the contrast medium.

Prior to the development of digital subtraction angiography, delivery of contrast media for performing film x-ray studies involved catheterization of the femoral artery. Generally this was accomplished using the Seldinger technique. The Seldinger technique involves the use of a sharp needle with a stylet extending therethrough, a long guide wire and one of several types of catheter, e.g. a pigtail catheter. Prior to performing the catheterization, the patient is prepped in the usual way by draping all of the patient except the area in the region of the femoral artery to be punctured. The skin of the patient is wiped with some type of preparation solution, such as alcohol or Betadine and then a small incision is made with a scalpel in the skin at the puncture site. The needle and stylet are then inserted through the incision in the skin until the stylet punctures both the front and back wall of the artery. Then the stylet is pulled out and the hollow tube and is pulled back slightly until the tip of it is in the artery as indicated by a substantial flow of blood from the tube.

Then a long guide wire is inserted through the tube into the artery and the tube is then pulled out of the artery leaving the guide wire in. The next step is to push the distal end of the guide wire completely through the length of the catheter, and then insert the proximal end of the catheter into the femoral artery over the guide wire. After the catheter is in place the guide wire is removed and the distal end of the catheter is connected to a syringe loaded in a power injector for delivery of contrast media to the artery.

The development of digital angiography and in particular digital subtraction angiography offers the potential of performing angiographic and arteriographic studies on an out-patient basis. Since high quality studies can be performed with substantially lower concentrations of contrast media, digital angiography can be performed using intravenous injection rather than intra-arterial injection of the contrast media. There are a number of prior art techniques which have been utilized for venous catheter placement. The jugular or subclavian vein catheter placement location, while permitting proximate catheter access to the superior vena cava for delivery of a tight bolus of contrast media, involve delicate and difficult procedures with possible substantial, dangerous complications and thus could not serve as an out-patient catheter insertion technique. Percutaneous insertion of the catheter into an antecubital vein is the method of choice, but up to now no combination of instruments and methodology has been provided for making antecubital vein catheter placement a sufficiently simple technique for a digital angiography to be performed on an out-patient basis.

Percutaneous insertion of the catheter into the antecubital vein generally involves the use either of a short catheter-over-needle arrangement or a catheter through catheter placement technique. The catheter over needle placement technique utilizes a catheter which is three or four inches long and has a tapered proximal end with a sharp needle or stylet extending through the proximal end aperture. The needle or stylet is inserted into a antecubital vein, after which the needle or stylet is withdrawn and the catheter pushed a distance of two or three inches into the vein. While this is a relatively painless and easy procedure to perform on an out-patient basis, the short catheter does not permit delivery of a tightbolus of contrast media due to the large capacitance involved in the venous structure of the patient's arm. Moreover, a very painful extravazation (leakage of fluid under the skin) can occur during power injecting of contrast media through a short venous catheter. Finally, no convenient kit of instruments has been provided for making the overall procedure, including periodic infusion of the catheter with a saline solution to preclude formation of blood clots or emboli in the catheter, one of simplicity and convenience for the patient and attending medical personnel.

There does not exist any auxilliary equipment in kit form which readily facilitates the supply of intravenous fluid to the catheter both before and subsequent to the delivery of contrast media through the catheter into the blood vessel. To accomplish this the distal end of the catheter must constantly be connected and reconnected to various fluid systems, representing a substantial inconvenience and source of error for the physician and other attending personnel.

Another approach that has been taken to placement of a central venous catheter using antecubital catheter insertion involves the use of a combination of a catheter over needle assembly to provide an initial cannulation of the vein, after which the needle is withdrawn from the catheter and a separate long catheter and guide wire combination are inserted through the short catheter already in position in the vein. While this technique provides for deep venous delivery of the contrast media the use of two catheter systems make the catheter placement procedure rather cumbersome and complex. Moreoever, the size of the long catheter which can be inserted through the short catheter is limited to a three French catheter size. In addition, there are no auxilliary components readily available to make it convenient to deliver intravenous fluid through the catheter both prior to and subsequent to the delivery of contrast medium using a power injector.

From the above discussion, it should be apparent that while there are a number of catheter placement techniques which could be used for digital intravenous angiography, prior to the development of the system covered by the above-referenced Enzmann and Brody patent application, the art had not provided a system for providing both an easy, almost painless catheterization of the antecubital vein for delivery of contrast media and other components and connections.

It is the principal object of this invention to provide an improved system for percutaneous introduction of a catheter into a major blood vessel of a human patient following the general principles of the Enzmann and Brody system.

In accordance with one aspect, this invention features a kit of instruments for percutaneous introduction of a catheter into a major blood vessel of a human patient which employs a hollow needle assembly having a proximal end to be inserted through the skin of a patient into the blood vessel, a guide wire adapted to be inserted through the needle into the blood vessel and a catheter having a proximal end adapted to be inserted into the blood vessel over the guide wire after the needle is withdrawn over the guide wire. The hollow needle assembly includes a first small gauge hollow needle having a beveled needle point on the front end thereof and at least a second hollow needle mounted concentrically over the first needle and having a sharp chisel-shaped front edge located a moderate distance behind the point on the first needle. The needle assembly is thereby adapted to be inserted relatively painlessly through the skin of the patient until the point of the first needle has pierced the blood vessel and the point of the second needle has pierced the skin of the patient to produce an enlarged skin opening for admitting the catheter therethrough. Preferably the hollow needle assembly includes a third hollow needle mounted concentrically over the second needle and having a sharp chisel-shaped front edge located a short distance behind the point on the second needle. The third needle is adapted to further enlarge the skin opening as the needle assembly is inserted through the patient's skin.

In a preferred embodiment the needle assembly further comprises a pair of outboard wings mounted over one of the needles and adapted to be readily grasped for inserting the needle into the blood vessel. A transparent backbleeding evaluation housing is mounted to the rear of the needle assembly. This housing has an internal chamber communicating with the interior bore of the first needle and is adapted to be filled with blood from the blood vessel when the point of the needle assembly is inserted therein. The backbleeding chamber has a rear port adapted to admit the guide wire for insertion through the internal bore of the needle into the blood vessel. A hydrophobic filter element is sealed into the rear port to permit air within the internal chamber to escape therefrom as the blood enters from the blood vessel. The filter element is a thin membrane readily piercable by the guide wire to admit the guide wire into the internal chamber without substantial loss of blood therefrom.

In a kit adapted for use in digital radiography a connector means is provided at the distal end of the catheter having at least a pair of fluid inlet ports adapted to be connected to first and second feed lines for introduction of first and second fluids into the blood vessel through the catheter. Each of the inlet ports have a one way valve means mounted thereto. This one way valve means has entrance and exit ports and a one way valve mechanism for permitting passage of fluids through the valve mechanism only when the fluid pressure at the entrance port of the valve exceeds the fluid pressure at the exit port.

In accordance with another aspect of this invention, a kit is provided in which the guide wire is substantially shorter than the length of the catheter. The catheter has a proximal end with a tapered wall section thereat and an in fluid inlet aperture and a plurality of separate fluid apertures located in the side wall thereof at a moderate distance from the proximal end. A guide wire lead aperture is formed in the side wire of the catheter a moderate distance behind the fluid outlet apertures and at an angle directed toward the end aperture to enable the distal end of the guide wire to be inserted into the end aperture and the guide wire lead aperture before inserting the catheter into the blood vessel.

The kit of this invention provides a simple to perform and relatively painless procedure for introducing a catheter into a vein or artery of the human body. A system of this invention can readily be applied to placement of a catheter for the purposes of central venous pressure measurement or a total intravenous feeding as well as other intravenous therapies requiring deep catheter placement. The catheter placement system of this invention is considerably less troublesome for the patient and involves fewer risks of complication than the techniques involving subclavian or jugular vein introduction of the catheter for the same purposes.

The overall system of this invention is particularly advantageously used in the performance of digital angiography procedures. The provision of the kit of instruments provided in accordance with this invention makes venous catheter placement a simple, painless procedure which should permit the use of digital angiography as an outpatient procedure and thus should greatly enhance the utility of digital radiography for screening patients with possible vascular diseases and pathology. The kit provided in accordance with this invention gives the physician and other hospital personnel in attendance during the procedure a simple one-time hook up of an IV fluid system and a contrast media delivery system to the catheter using a branching connector arrangement with a valve for controlling the flow of the fluids into the catheter. This provides further simplification of the overall procedure for performing a digital angiography providing a continuous infusion of intravenous fluid both prior to and subsequent to the delivery of contrast media from a power injector system. The system of this invention thus provides maximum convenience for the attending hospital personnel and minimum discomfort and risks for the patient on which the procedure is being performed.

Other objects, features, and advantages of this invention will be apparent from a consideration of the following detailed description taken in conjunction with the accompanying drawings.

FIGS. 1-4 illustrate two embodiments of a hollow needle assembly which is one component of a kit in accordance with this invention. The specific embodiment disclosed in FIGS. 2-4 constitutes an improvement over the embodiment shown in FIG. 1 and is covered in the above-referenced Enzmann and Brody patent application.

Figure 1:
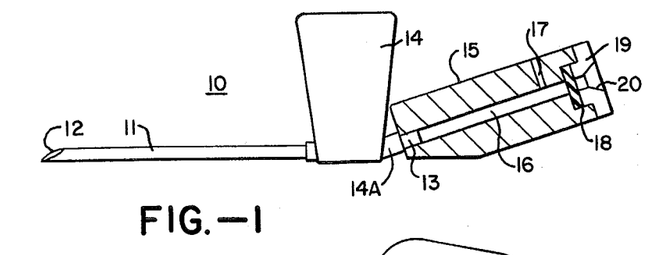
FIG. 1 is a partly sectioned elevational view of a hollow needle and backbleeding evaluation chamber forming one component of a catheter insertion system in accordance with the Enzmann and Brody system.

FIG. 1 depicts a hollow needle assembly 10 which includes a hollow needle 11, a pair of flexible outboard wings 14 mounted near the distal end 13 of the needle 11 and a backbleeding evaluation chamber 15 mounted at the distal end 13 of the needle assembly. The needle 11 has a sharp proximal end 12 adapted for relatively painless insertion of the small gauge needle into a major blood vessel of the patient. Backbleeding evaluation chamber 15 generally comprises a hollow transparent housing having an internal chamber 16 therein communicating with the internal bore of needle 11. One or more small capillary apertures 17 may be formed between the internal chamber 16 and the outer surface of the housing 15 to permit escape of air from the internal chamber 16 as it fills with blood. The capillary aperture 17 is sized to permit escape of air but to be too small to allow any substantial blood flow out of the internal chamber 16.

A piercable membrane valve member 18 cooperates with an end cap 19 having a tapered aperture 20 therein to permit a small diameter guide wire to be inserted through valve member 18 into the internal chamber 16 and thence into the internal bore of the needle 11. The end cap 19 may be cemented or ultrasonically welded onto the front of backbleeding housing 15. The valve member 18 may simply be a piercable membrane or a flap-leaf valve which seals around a guide wire after it is inserted through the needle assembly.

The outboard wings 14 are generally molded from a flexible plastic material having a central hub portion 14A which slips over the exterior of the hollow needle 11. The front end of the backbleeding housing 15 may be secured in any conventional fashion to the distal end 13 of the hollow needle or to the hub of the outboard wing 14. A short section of tubing may be used to connect the needle to the backbleeding chamber, if desired. Means such as an adhesive or ultrasonic welding of plastic parts may be utilized. The backbleeding housing 15 is preferably molded from a transparent plastic material so that the presence of blood in the internal chamber 16 can readily be visualized. When provided as a part of a kit of instruments in accordance with this invention, the sharp point 12 of the needle 11 will generally be protected by a plastic sheath. The needle assembly will be sterilized prior to placement in the kit by using a conventional sterilization process.

Figure 2:
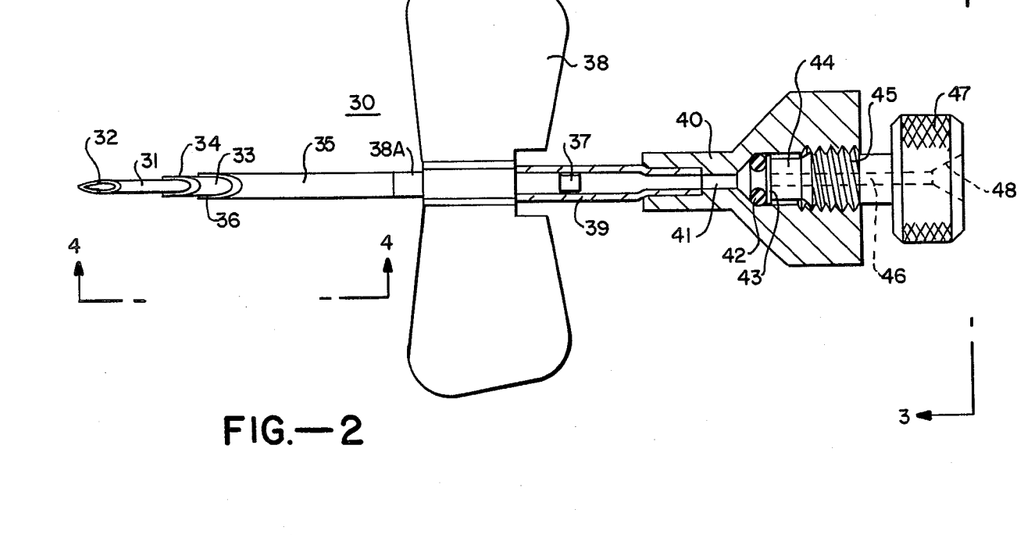
FIG. 2 is a partly sectioned top view of a hollow needle assembly including a backbleeding evaluation chamber in accordance with this invention.
Figure 3:
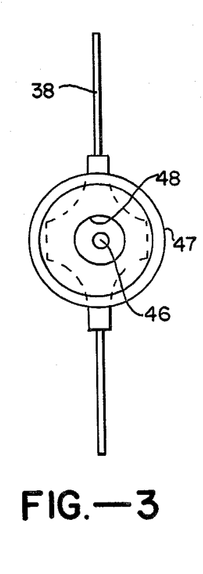
FIG. 3 is a end view of the needle assembly of FIG. 2 taken along the lines 2—2.
Figure 4:
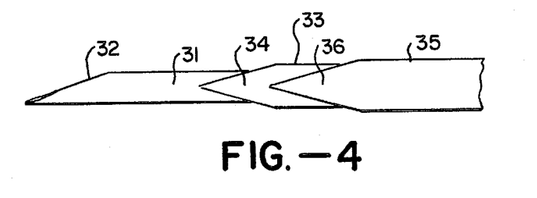
FIG. 4 is an enlarged side view of the needle assembly of FIG. 2 taken along the lines 4—4 in FIG. 2.

Referring now to FIGS. 2-4, an improved hollow needle assembly 30 which employs the general principles of this invention but is especially covered by the above-referenced Enzmann and Lundquist patent application will be described. Needle assembly 30 comprises three separate hollow needles 31, 33, and 35 assembled together in concentric manner. However, it should be understood that only two concentric needles could be used for the same purpose. A sharp point 32 on inner needle 31 is provided for initial piercing of the skin and blood vessel of the patient. Intermediate needle 33 has a sharp chisel point 34 spaced a moderate distance behind point 32 on needle 31. Correspondingly, the sharp chisel point 36 on the outside needle 35 lies a short distance behind the chisel point 34 on intermediate needle 33. As will later be seen the purpose of the coaxial arrangement of the three needles as shown in FIG. 2 with the point arrangement shown in enlarged scale in FIG. 4 is to produce a vein puncture site (or arterial puncture site) wherein the skin flap produced by insertion of the needle beyond the point 36 of the outer needle is enlarged to permit ready passage of a catheter having an outer diameter substantially commensurate with the outer diameter of the outside needle 35. The staggered needle points 32, 34, and 36 enable relatively painless insertion of the needle through the skin of the patient, producing an enlarged aperture in the skin which permits relatively painless passage of the catheter through the puncture site. The intermediate needle 33 and outer needle 35 should be tight fitting to avoid any painful trapping of skin between the concentric coaxial needles. The intermediate needle 33 and the outer needle 35 may be secured in place over the inner needle 31 using any conventional approach such as the use of an epoxy adhesive or tack welding of the items together.

The outboard wings 38 are preferably molded from a flexible plastic material having a central hub 38A which fits over the outer needle 35 in either a tight fitting engagement or with an adhesive securing of the plastic hub 38A over the outer needle 35. Alternatively the hub 38A of the outboard wings can be mounted over either the intermediate needle 33 or the inner needle 31, again using any conventional means for securing the plastic hub 38A on the exterior surface of one of the needles.

A transparent plastic backbleeding housing 40 is mounted to the distal end 37 of the hollow needle portion of the needle assembly 30 by means of a section 39 of flexible plastic tubing. The tubing 39 may be secured to the hub 38A of the outboard wings 38 or to one of the three needles using any conventional securing means. The hollow tube 39 communicates blood from the internal bore of the needle 32 into an internal chamber 41 of the backbleeding housing 40, thus together forming a backbleeding evaluation chamber. Mounted within backbleeding housing 40 is an O-ring sealing valve 42 and a hydrophobic filter element 43 in the form of a thin disk. As shown in FIG. 2 a hollow valve screw 45 holds the piercable hydrophobic filter 43 tightly against the O-ring 42 to provide a fluid tight seal. The hydrophobic filter 43 permits the escape of air from the internal chamber 41 of the housing 40 through the bore 46 of the valve screw 45 and out the rear port 48. A knob 47 is provided on the valve screw 45 to assist in turning it into the threaded portion of the housing 40. The tapered aperture 48 on the front of the screw head 47 facilitates introduction of a thin guide wire through the internal bore 46 of the valve screw 45. The guide wire readily pierces the hydrophobic filter membrane 43 to enter the internal chamber 41 of housing 40 and the interior of hollow tube 39 for insertion through the internal bore of the needle 31. The hydrophobic filter 43 precludes any substantial loss of blood from the internal chamber 41 and the hollow tube 39 after being pierced by the guide wire.

Numerous other approaches could be taken to securing the hydrophobic filter membrane 43 and the O-ring 42 within the housing 40. For example, a hollow plastic end cap could be ultrasonically welded in place with application of axial pressure on the hydrophobic membrane 43 and the O-ring 42 to provide a tight seal. Numerous other approaches could also be taken to providing a valve element on the back end of a backbleeding chamber of the type shown in either FIG. 1 or FIG. 2 to provide a fluid tight seal but readily admit a thin guide wire for introduction through the needle assembly. For example, in combination with a capillary size air vent hole, an O-ring and compression screw arrangement could be provided with the compression screw arrangement initially compressing the O-ring into a sealed flat disk configuration, preventing the leakage of blood through the interior of the O-ring. Introduction of the guide wire could then be accomplished by inserting the front end of the guide wire through the compressing screw and then gradually backing off on the compression of the O-ring until the guide wire fits through the aperture in the O-ring without permitting any substantial loss of blood from the internal chamber of the back bleeding evaluation housing.

It should be apparent that it would be possible to use only a single coaxial needle 33 on the front end of the needle assembly 30, or alternatively, more than three coaxial needles could be provided depending on the size of the skin puncture desired for admission of a particular size of catheter through the puncture site.

Preferably the needle section 11 in FIG. 1 and the inner needle 31 in FIG. 2 are 19 gauge needles. The length of the needle and in particular the distance between the tip 32 and the cutting edges 34 and 36 in FIG. 2 is tailored to the application, i.e., whether the needle is to be used for venapuncture or arterial puncture. For a venapuncture needle, the distance from the tip of point 32 to the tip of point 34 is preferably about 0.25 inch and the distance between the tip of point 32 to the tip of point 36 should be about 0.35 inch. The chisel cutting edges 34 and 36 are preferably formed at about a 15° angle to the exterior surface of the associated needle forming a total 30° included angle of the chisel point.

Figure 5:
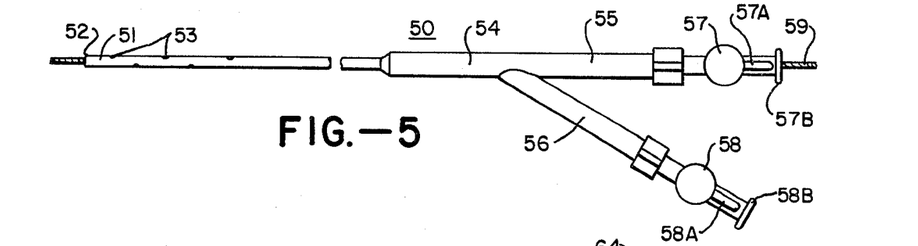
FIG. 5 is a side elevational view of a catheter and valve assembly in accordance with the Enzmann and Brody system.

FIG. 5 illustrates one version of a catheter-connector and valve assembly forming a second component of a kit of instruments in accordance with the Enzmann and Brody system. The front end 51 of the catheter assembly 50 is a small hollow catheter which is relatively soft and flexible but allows for an internal flow rate of contrast media of up to 45 cubic centimeters per second. Preferably the proximal section 51 is a four or five French catheter having side holes 53 spaced a moderate distance behind the end aperture 52. A distal branching connector section 54 is provided on the catheter assembly 50 and has two inlet port arms 55, 56. Connected to each of the inlet port arms 55, 56 is a stopcock valve 57, 58 having single inlet and outlet ports. The stopcock valve 57 permits the traverse of a small gauge guide wire 59 through the entire length of the catheter if a long guide wire is utilized in the kit. Valve actuators 57A and 58A are used to control the open or closed state of the valve and Luer fittings 57B, 58B are provided at the inlet ports of the valves 57, 58. This enables a good fluid tight Luer lock coupling to be made between the valves 57, 58 and tubing leading to separate fluid sources. Other valve arrangements for separately controlling the introduction of fluid into the connector section 54 of the catheter assembly 50 could obviously be provided.

Figure 6:
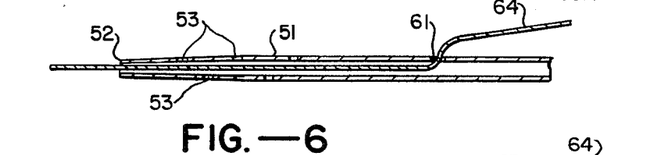
FIG. 6 is a section view of the proximal end of a catheter in accordance with this invention.
Figure 7:
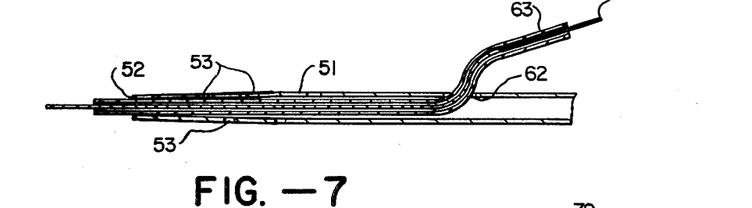
FIG. 7 is a section view of the proximal end of a catheter in accordance with this invention.

FIGS. 6 and 7 illustrate alternative versions of a general arrangement for providing a means for threading a shorter guide wire 64 through only a portion of the proximal end 51 of a catheter assembly. FIG. 6 illustrates the approach of this invention to provide a short guide wire and threading arrangement. A guide wire threading aperture 61 formed at a large angle to the wall of the catheter is provided a moderate distance behind the side apertures 53 in the proximal section 51 of the catheter. This enables the threading of the short guide wire 64 through the end hole 52 of the catheter and the guide wire threading aperture 61. This is facilitated by bending the catheter at the position of the guide wire aperture 61 until the axis of that aperture is parallel to the center line of the front section of the catheter so that the guide wire 64 can easily be threaded first into the end hole 52 and then out the guide wire aperture 61. As will later be seen this readily facilitates the placement of the guide wire in the catheter and advancing of the catheter over the guide wire into the blood vessel of the patient.

FIG. 7 shows an alternative arrangement in accordance with the Enzmann and Brody system. In the FIG. 7 embodiment the guide wire aperture 62 receives a guide tube 63 which extends through that aperture and the proximal tip of the catheter and out the end hole 52. The guide tube 63 readily guides the coiled wire guide wire 64 through the end hole 52 and the guide wire aperture 62. As will later be seen this permits the catheter to be inserted into the blood vessel of the patient over the guide wire and thereafter the guide wire 64 and the guide tube 63 may be removed from the catheter so that it can be advanced further into the blood vessel.

Figure 8:
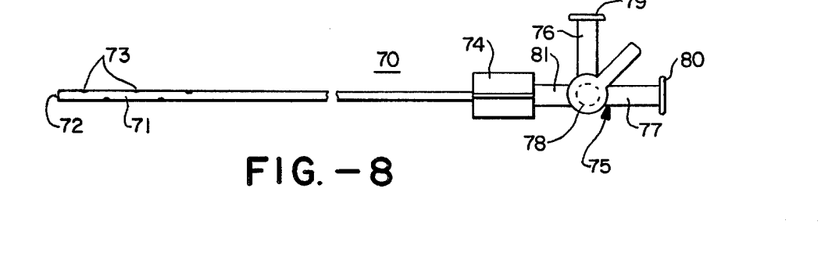
FIG. 8 is a elevational view of a catheter and valve assembly in accordance with this invention.

FIG. 8 depicts a version of a catheter and valve assembly 70 in accordance with this invention. In this embodiment the catheter 71 comprises a commercially available catheter having a screw fitting 74 adapted to receive a threaded stopcock valve arrangement 75 in a fluid sealing engagement. Generally this is accomplished with a flared end on the catheter 71 mating with a flared end on the threaded outlet port 81 of the stopcock valve 75. The proximal end of the catheter 71 preferably includes one of the short guide wire feeding approaches depicted in FIGS. 6 and 7 but may also use the long guide wire, total catheter threading approach depicted generally in FIG. 5. The stopcock valve 75 includes two inlet ports 76, 77 each having a Luer fitting 79, 80 thereon. A valve actuator 78 controls the admission of fluid through one of the inlet ports 76, 77 or closes off both ports under manual control.

The long guide wire 59 depicted in FIG. 5 and the short guide wires 64 depicted in FIGS. 6 and 7 are preferably a standard coiled wire type of guide wire having a diameter of about 0.025 inches. The length of the guide wire depends on the guide wire threading technique and the catheter length. Generally, the preferred catheter length in accordance with this invention is one sufficient to permit the proximal end of the catheter to reach the superior vena cava of the patient and this will generally involve a catheter of 50 to 60 centimeters. As previously indicated the catheter should be soft and flexible so that it is readily inserted through the antecubital vein of the patient into the superior vena cava. In addition, it is preferable that at least the tip of the catheter be radioopaque so that its placement in the superior vena cava can be verified by a fluoroscopy. The provision of multiple side holes allows rapid injection of a volume of contrast medium and the deep venous placement of the catheter will permit the delivery of a tightbolus of 50 to 60 cubic centimeters in a 2 or 3 second delivery period from a power injector. The catheters depicted in FIGS. 5 and 8 are particularly adapted for venous catheter placement. However, for arterial catheter placement a pigtail catheter, i.e., a catheter having a curled front end could be employed to make it easier to advance the catheter through the arterial structure of the patient.

Figure 9:
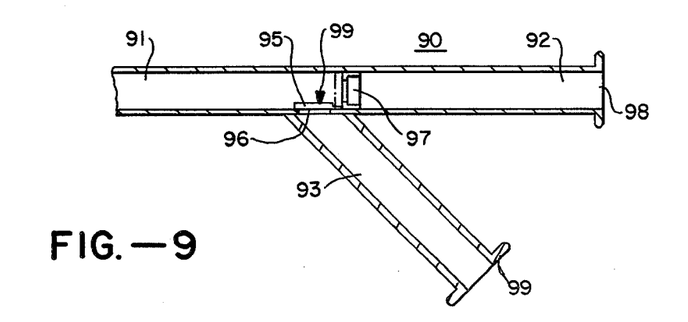
FIG. 9 is a partial view of a branching connector and integral flap valve portion of a catheter assembly in accordance with the Enzmann and Brody System.

FIG. 9 depicts a branching connector section 90 in accordance with the Enzmann and Brody system and having an integral flap valve 94 at the branch location between the inlet arms 92 and 93. This branching connector section 90 may either be formed directly on the catheter by joining the outlet section 91 to the thinner flexible catheter or may be separately connected to the catheter by using a standard Luer fitting arrangement. The integral flap valve mechanism 94 includes a hinged valve element 95 having a first valve position (shown in solid lines) which occludes the opening 96 to the inlet arm 93. A second valve position (shown in dashed lines) causes the valve flap 95 to occlude the aperture 97 in the inlet arm 92. Each of the inlet arms 92, 93 has a Luer fitting 98, 99 thereon for connecting the inlet arms to fluid delivery tubes leading to separate fluid sources. The integral valve arrangement depicted in FIG. 9 is especially advantageously employed with the fluid inlet arm 92 connected to a source of intravenous fluid for continuous flushing of the catheter while it is inserted in the blood vessel of the patient and with the fluid inlet arm 93 coupled by way of a feed tube to a syringe containing contrast media to be injected by means of a power injector apparatus. The pressure from the intravenous fluid delivery system coupled to inlet arm 92 will maintain the flap valve 95 in its first valve position. When the power injector is operated to deliver contrast media under pressure to inlet arm 93, the flap valve 95 will automatically be positioned to block the flow of any contrast media back into the intravenous fluid delivery system through inlet arm 92. This integral valve and connected assembly could also be utilized with connections to two separate power injectors for sequential delivery of volumes of contrast media through the catheter into the patient.

Figure 10:
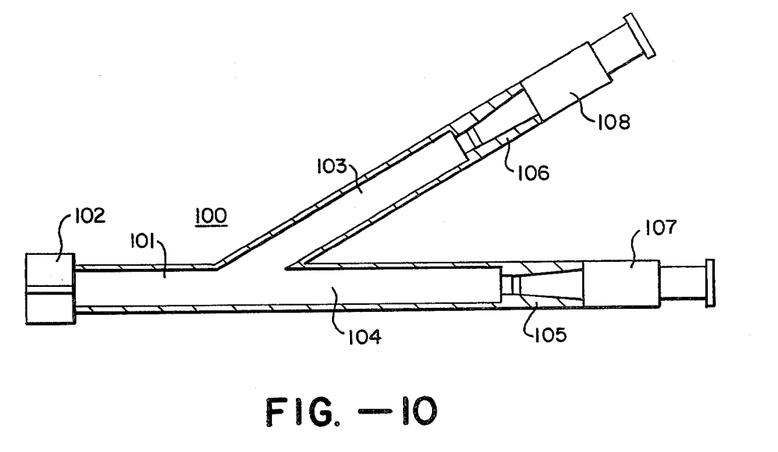
FIG. 10 is a sectioned elevational view of a branching connector assembly in accordance with this invention.

FIG. 10 depicts a version of a branching connector and valve arrangement 100 in accordance with this invention. As shown in FIG. 10 a branching connector 100 has a outlet arm 101 having a connector arrangement 102 adapted to mount the branching connector to the Luer fitting 80 on the stopcock valve 75 shown in FIG. 8. The branching connector assembly 100 has a straight through fluid inlet arm 104 and a branching fluid inlet arm 103. On the inlet end 105 of fluid inlet arm 104 a one way valve arrangement 107 is mounted. On the inlet end 106 of the fluid inlet arm 103 a second one way valve 108 is provided.

Figure 11:
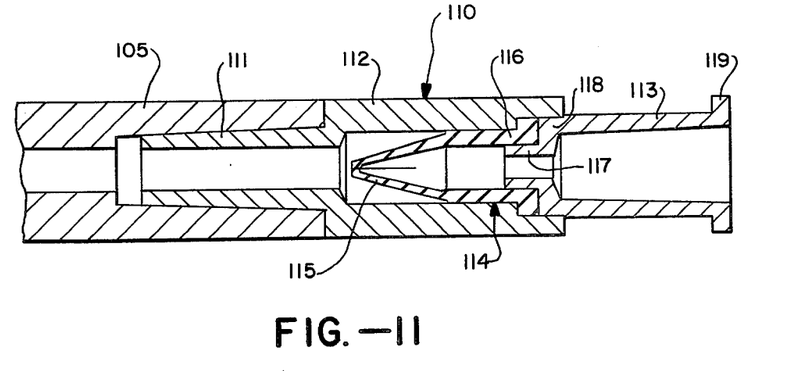
FIGS. 11 and 12 are sectioned elevational views of one way fluid valves useful in the branching connector assembly depicted in FIG. 10.

FIGS. 11 and 12 depict alternate versions of one way valves which may be incorporated into the connector valve arrangement 100 shown in FIG. 10. In FIG. 11 a one way valve arrangement 110 is depicted. One way valve 110 comprises a generally hollow housing having an elongated exit port section 111 which mates with the end 105 of fluid inlet arm 104 in a fluid tight sealing engagement. Preferably these components are ultrasonically welded together or adhesively secured to preclude blowing the one way valve 110 out of the connector arm 104 under high counter-flow pressure. Valve housing section 112 provided on the one way valve 110 has an open front end receiving a duckbill valve 114. Entrance port section 113 of one way valve 110 has a first nose section 117 which mates with the inlet port section 116 of duckbill valve 114 and a second nose section 118 which mates with the front end of the valve housing 112 to retain the duckbill valve 114 in the valve housing section 112. The second nose section 118 is secured to the valve housing section 112 in any conventional manner, such as by ultrasonic welding or using an appropriate adhesive. The duckbill valve 114 has a duckbill section 115 which hinges to permit fluid to flow in one direction when the pressure to the right of the hinged duckbill is higher than the pressure to the left of the duckbill 115. When the pressures are reversed the higher pressure outside the duckbill valve keeps the flapped valve section 115 closed, precluding counter flow of fluid. A very tight and complete sealing of the duckbill valve 114 within the valve chamber 112 is required when high pressure in the counter-flow direction of the valve is anticipated. Duckbill valves of the type shown are available from Moxness Products Corporation of Racine, Wis.

Figure 12:
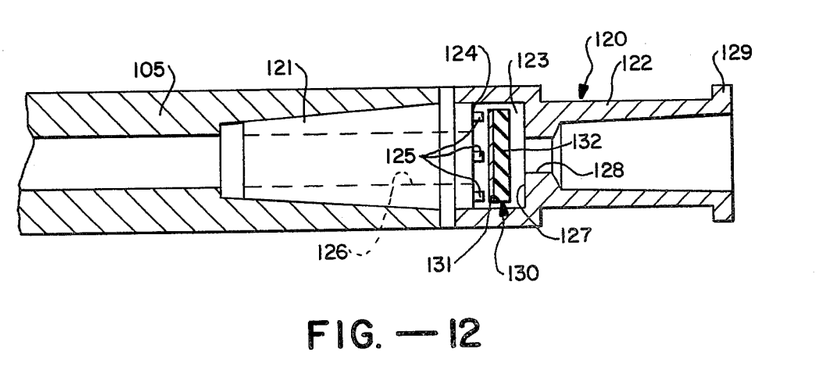
Figure 13:
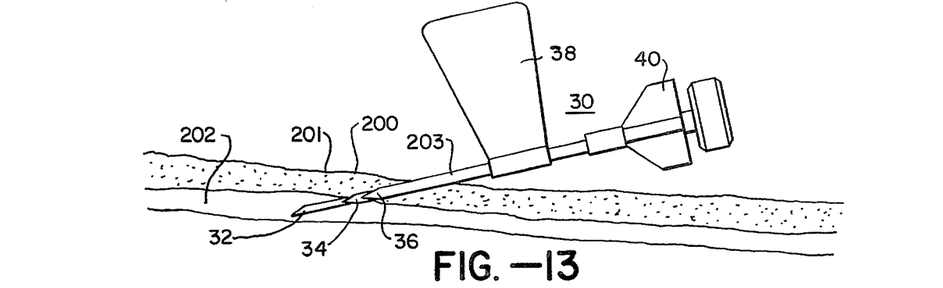
FIGS. 13-18 depict a catheter insertion method in accordance with the Enzmann and Brody system utilizing instruments from a catheter placement kit in accordance with this invention.

FIG. 12 illustrates the structure of another type of one way flow control valve 120. In this case the flow control valve 120 is an improved version of a one way valve available from Burron Medical, Inc. of Bethlehem, Pa. as Burron Part No. S-540-1000L. This one way valve has a hollow inlet valve section 122 and a hollow outlet valve section 121 which are adapted to mate together to form a hollow valve chamber 123. The outlet valve section 121 mates with and is secured to the inlet port section 105 of the branching connector 100 shown in FIG. 10. Outlet valve section 121 has a non-sealing valve face 124 with a plurality of separated posts 125 disposed around fluid port 126 and extending into valve chamber 123. Inlet valve section 122 has a sealing valve face 127 with a fluid inlet port 128 communicating therewith. A disk shaped valve element 130 is mounted within valve chamber 123 and comprises a sandwich of a thin metal disk 131 and a thin disk of resilient material 132. Metal disk 131 faces the outlet valve section 121 and provides sufficient rigidity to the valve element 130 to preclude collapse of the valve element 130 into the outlet port 126 under high pressure and flow of fluid in the inlet section 122. Moreoever, the thin metal disc 131 provides sufficient rigidity to the valve element 130 to preclude it being blown through the inlet port 128 under the influence of a high counterflow fluid pressure. Thus the sandwiched valve element 130 permits the one way valve to operate with relatively high fluid pressures in both the flow admitting direction and the flow blocking (counterflow) direction of the valve. This is especially important when the one way valve is to be used with a power injector for contrast media since substantial pressures are involved in rapid delivery of the bolus of contrast media.

Figure 17:
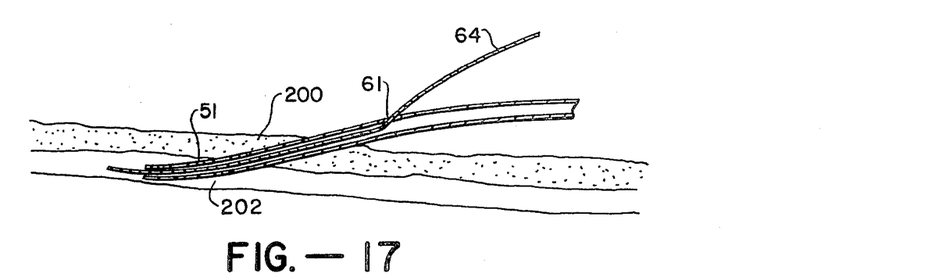
Figure 18:
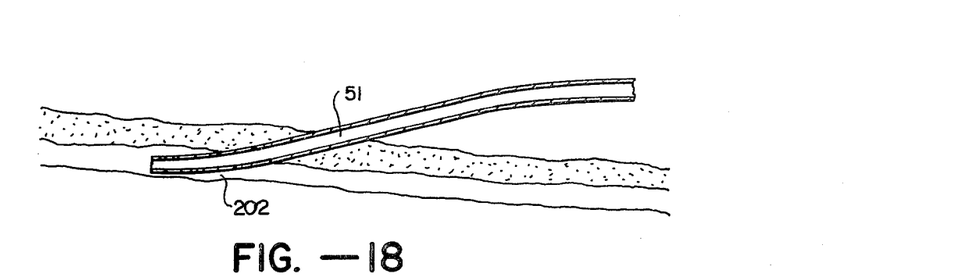
Figure 19:
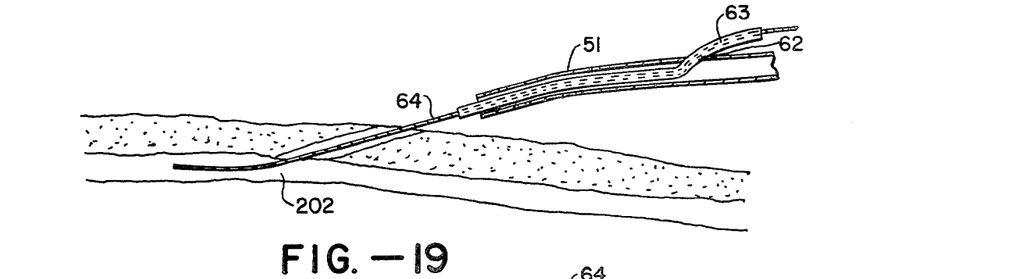
FIGS. 19-20 depict alternate versions of certain steps in a catheter placement method in accordance with this invention using an alternative catheter structure.
Figure 20:
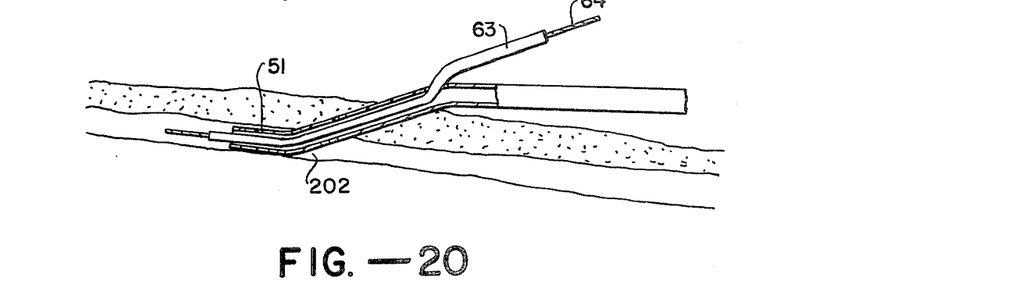

FIGS. 13-18 illustrate the method of the Enzmann and Brody invention for introducing a catheter into a major blood vessel of a human patient by using the kit of instruments described above. The method is generally illustrated using the preferred components of the kit in accordance with this invention, namely the needle assembly shown in FIGS. 2-4 and the short guide wire feeding arrangement shown in FIG. 6. FIGS. 19 and 20 illustrate optional use of a catheter having the short guide wire feed arrangement depicted in FIG. 7 of the drawing. The use of the hollow needle assembly of FIG. 1 as an alternative to that depicted in FIG. 2 will be apparent from the description given of FIGS. 13-18. FIGS. 13-18 are generally intended to represent introduction of a catheter into a major blood vessel of a human patient and the description given will be in conjunction with an intravenous catheter placement using the antecubital vein at the elbow of a patient. It should be understood however that the apparatus and method of this invention could also be employed to place a catheter in a major artery of a human patient such as the femoral arterial catheter placement depicted in FIG. 25 of the drawings.

Figure 14:
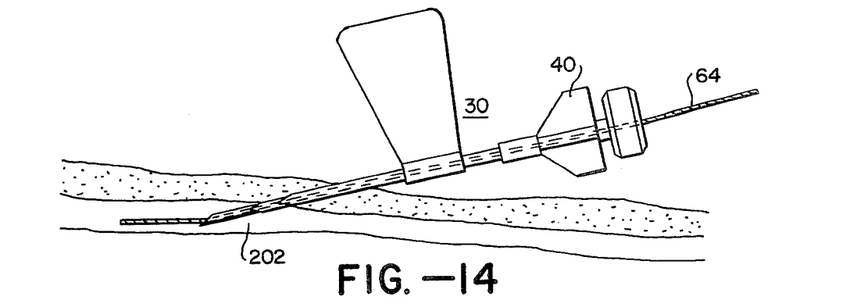

The catheter placement method of the Enzmann and Brody invention utilizing a kit of instruments of this invention involves first the step of performing a venapuncture utilizing the hollow needle assembly 30. First the arm of the patient is draped with a sterile drape (not shown) having a window at the venapuncture site 203. The area of the venapuncture site is swabbed with a standard preparation solution. Then the tip 32 of the needle assembly 30 is inserted through the skin of the patient 201 into the blood vessel 202, in this case an antecubital vein. The auxilliary cutting edges 34 and 36 on the needle assembly 30 enlarge the skin opening. Proper insertion of the needle tip 32 into the blood vessel 202 is indicated by blood flowing back through the bore of the needle into the backbleeding evaluation chamber 40. Insertion of the needle is readily accomplished in a relatively painless manner by the grasping of the flexible outboard wing section 38 and manipulating the needle through the skin until the vein 202 is punctured. Once punctured the vein has been verified, the guide wire 64 may be introduced into the vein 202 through the hollow needle assembly 30. This is accomplished by pushing the front end of the guide wire 64 through the entire length of the hollow needle assembly 30 and a short distance into the vein 202 as depicted in FIG. 14.

Figures 15, 16:
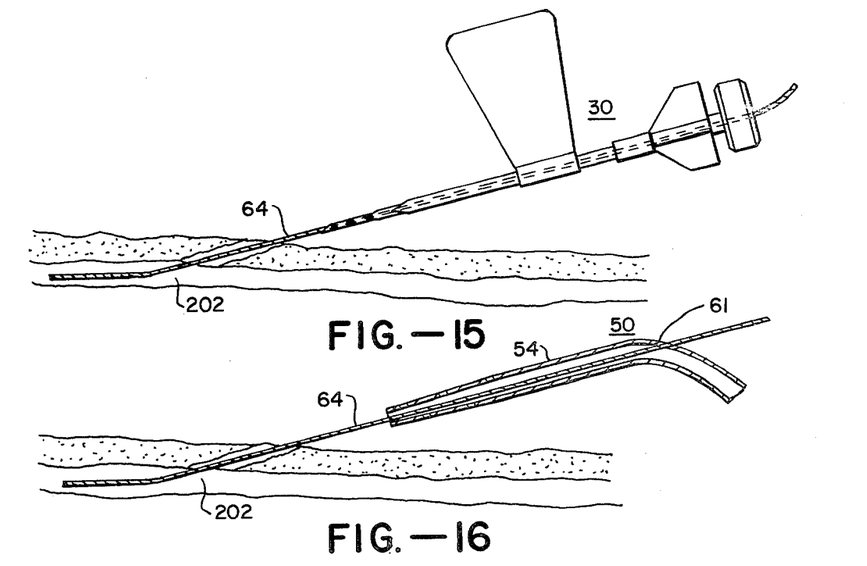
Figure 21:
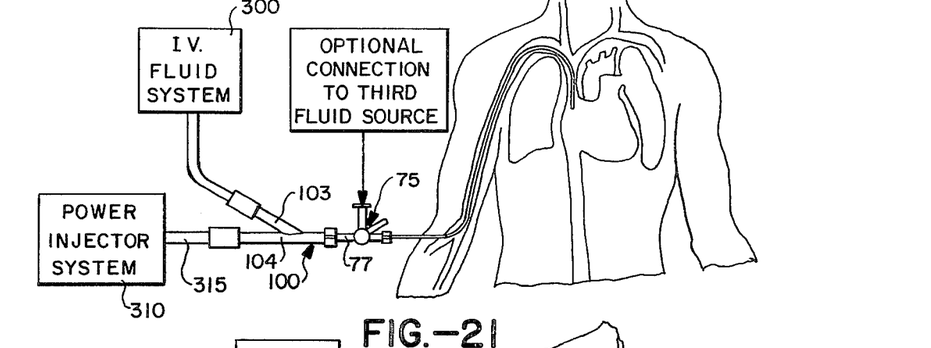
FIG. 21 depicts an overall set up utilizing a kit embodying principles of this invention to perform digital intravenous radiography on a human patient.

Then, as depicted in FIG. 15, the hollow needle assembly 30 is withdrawn over the guide wire 64 with gentle pressure being applied to the vein where the guide wire lies within it to be sure to retain the guide wire in the vein. The next step is as shown in FIG. 16 and involves threading the guide wire 64 through the proximal end section 51 of the catheter 50, bending the catheter at the point of the guide wire threading aperture 61 to enable the guide wire to exit the catheter at that point. The proximal end of catheter 50 may also be provided with a preformed curve to insure proper threading of the guide wire. Thereafter, the proximal end of the catheter 51 is advanced into the vein 202 as depicted in FIG. 17. Partial advancement of the proximal end 51 of the catheter is accomplished at this time until the tip of the catheter is in the vein but the guide wire threading aperture 61 lies outside the surface of the skin 200 of the patient. At this point the catheter 51 is held in place in the vein while the guide wire 64 is withdrawn leaving the tip of the catheter in the vein as depicted in FIG. 18. Next the catheter is pushed further into the vein 202 until its proximal tip extends into the superior vena cava of the patient as depicted in FIG. 21. If the catheter has a preformed curve at the proximal end this positioning of the end in the superior vena cava will be facilitated.

FIG. 19 depicts the alternative technique of threading the guide wire 64 through a guide tube 63 extending through guide wire aperture 62 in the side wall of the proximal section 51 of catheter 50. Thereafter, the catheter 51 is inserted into the vein 202 as depicted in FIG. 20, after which the guide tube 63 and guide wire 64 may be removed and the catheter fully advanced through the vein until the tip is lodged in the superior vena cava.

After the catheter is in place, a syringe is attached to the back of the catheter at the inlet port 77 of the valve 75 to draw blood into the catheter. Thereafter, the side arm 103 of connector 100 is connected to an intravenous fluid delivery system 300. Delivery of intravenous fluid may be performed using a standard IV drip or IV pump arrangement. Generally it is preferred to use a heperinized saline solution as the intravenous fluid to constantly infuse the catheter to keep blood from clotting therein. To perform a digital angiographic study, a syringe containing contrast media is mounted in a power injector 310 and a feed tube 315 from the power injector system 310 is coupled to the inlet arm 104 of the branching connector 100. Prior to connecting the branching connector 100 to the catheter, connections to the IV fluid and the power injector are made and all air is pushed out of the IV tubing, the injector tubing and the connector. Then the connector is connected to the catheter.

At this point, when the x-ray imaging system has been properly positioned for the particular study to be performed on the patient, the power injector can be operated to deliver a bolus of contrast media to the catheter.

If the one way valve type of branching connector shown in FIGS. 10–12 is utilized, during power injection of the contrast media the one way valve in the inlet arm 104 will open and, due to the pressure of delivery of the contrast media the one way valve in the inlet arm 103 for the intravenous fluid will close. After the power injection of contrast media is terminated and the pressure in the inlet arm 104 drops, the one way valve in the inlet arm 103 will automatically open again to continue infusion of intravenous fluid through the catheter.

FIG. 21 shows an optional connection to a third fluid source which may be made through the stopcock valve 75. This optional third fluid source may for example be another power injector for injection of a second bolus of contrast media. Manual repositioning of the valve element 75 would be required to admit this fluid to the catheter. The optional third fluid source may also be another intravenous fluid system which can be manually valved into the catheter either before or after pressure injection of contrast media. Stopcock valve 75 could also be used for a separate connection to a central venous pressure monitor.

It should be apparent that the branching connector 90 shown in FIG. 9 and having an integral flap valve could be also used with separate fluid connections to an intravenous fluid system and a power injector system. In that case a single two-position valve element controls the delivery of intravenous fluid and contrast media to the catheter with automatic closure by the valve of the port leading to the intravenous fluid when the power injector is operated to deliver contrast media to the inlet arm 93 of the branching connector 90.

Figure 22:
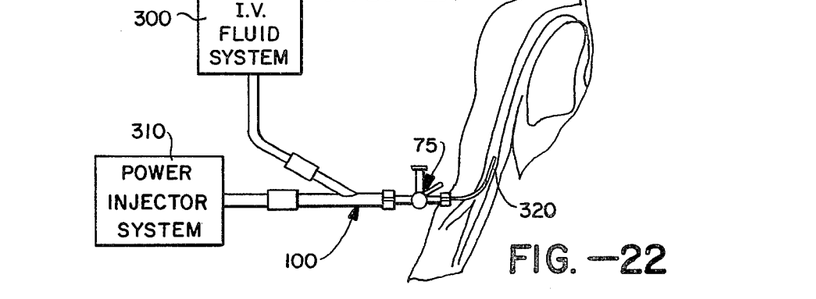
FIG. 22 depicts the overall set up of a kit of instruments for performing digital intravenous radiography utilizing novel components of a kit in accordance with this invention together with a short catheter-over-needle type of venous catheter placement.

FIG. 22 illustrates that the branching connector arrangement of this invention may also be utilized with a short intravenous catheter of the catheter-over-needle type 320 and still achieve many of the advantages of this invention. However, in this case the bolus of contrast media will not be as tightly confined because it is not delivered directly to the superior vena cava but instead must traverse a large capacitive area of the venous structure of the arm. It should of course be understood that the long catheter introduction approach of this invention could be utilized without inserting the catheter all the way to the superior vena cava if for some reason the vein structure of the patient precludes such deep insertion of the catheter. In all cases it is preferable that the catheter be placed deep within the patient for optimum delivery of a bolus of contrast media and to minimize the risk of extravazation which may occur if a weak spot in the vein should rupture.

Figure 23:
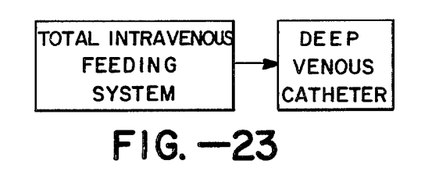
FIG. 23 is a block diagram showing the use of a catheter placement kit in accordance with this invention as part of a total intravenous feeding system.

FIG. 23 illustrates that the deep venous catheter kit of this invention can be utilized to advantage in a total intravenous feeding system. The simplicity and relatively painless character of the catheter introduction system and method of this invention with its attendant lower risk of complications to the patient should be a preferred technique over subclavian or internal jugular vein placement of a short intravenous catheter for total intravenous feeding.

Figure 24:
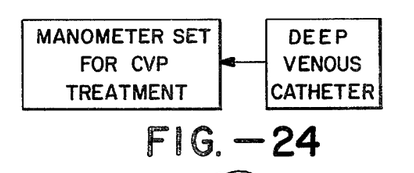
FIG. 24 is a block diagram depicting the use of a catheter placement kit in accordance with this invention for central venous pressure measurement.

FIG. 24 illustrates that the deep venous catheter kit of this invention may also be advantageously employed together with a pressure manometer set for performing central venous pressure measurements. Again the deep venous catheter placement system of this invention should be preferred over other techniques for inserting catheters into the superior vena cava for central venous pressure measurement.

Figure 25:
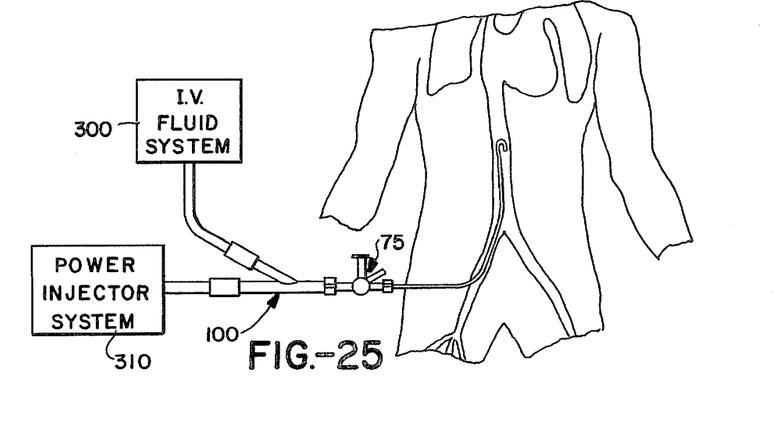
FIG. 25 depicts the overall setup for utilizing a catheter placement kit and method in accordance with this invention for digital radiography in which the catheter is placed in the femoral artery of the human patient.

FIG. 25 illustrates that the catheter placement system of this invention may also be employed to place a small diameter pigtail catheter in a large artery of the human patient. In FIG. 25 placement within the femoral artery with arterial puncture in the groin of the patient is shown. In some instances it may be preferable to inject contrast media directly into the aorta of the patient to improve the visualization of certain arterial regions of the body. In this case a catheter having a pigtail or curved end is preferred since it more easily traverses the arterial structure of the patient. It should be apparent that the catheter placement system of this invention could also be employed to introduce catheters into other major blood vessels of a human patient such as, for example, introduction into major veins of the leg.

While the catheter introduction system of this invention has been described above in connection with several embodiments, it should be understood that numerous modifications could be made by persons of skill in this art without departing from the scope of this invention. In addition, it should be understood that although various embodiments of a kit of instruments for introducing a catheter into a major blood vessel of a human patient and providing a valved-branching connector arrangement to plural fluid sources for use in digital radiography have been described, numerous changes and modifications could be made without departing from the scope of this invention.

We claim:

1. A connector assembly in combination with a catheter having a distal end adapted to be inserted into a major blood vessel of a human patient and a proximal end remaining outside said patient, comprising a branching connector having one outlet arm with an outlet port connected to said proximal end of said catheter and at least two inlet arms, each with an inlet port connected to first and second feed lines for introducing first and second liquids into said blood vessel through said catheter, each of said inlet ports having one-way valve means mounted therein, said one-way valve means having entrance and exit ports and means for permitting passage of liquid through said valve mechanism when the liquid pressure at said entrance port of said one-way valve means exceeds the liquid pressure at said exit port of said one-way valve means, each of said one-way valve means comprising generally hollow inlet and outlet valve sections mated to form a hollow valve chamber, said outlet valve section having a plurality of separate abutments disposed around said outlet port and extending into said valve chamber, said inlet valve section having a sealing valve face with an inlet port therein and a disc-shaped valve member mounted within said valve chamber and comprising a sandwich of a relatively thin relatively rigid disc and a relatively thick disc of relatively resilient material with said resilient material facing said inlet valve section, said relatively thin and relatively thick discs being congruent, said relatively rigid disc providing sufficient rigidity to said valve element to enable said one-way valve to operate with relatively high pressure in both the flow admitting direction and the flow blocking direction of the valve, said disc-shaped valve member having planar uninterrupted surfaces facing the inlet port and the outlet port.

2. The combination of claim 1 wherein said chamber is cylindrical in cross section and wherein said valve member has a circular configuration with a diameter substantially less than the diameter of the chamber.

3. The combination of claim 1 wherein the relatively thin rigid disc is formed of metal.

* * * * *